United States Patent [19]

Eibl et al.

[11] 4,276,259

[45] Jun. 30, 1981

[54] APPARATUS FOR PERFORMING A RADIOIMMUNOLOGICAL METHOD OF DETERMINING ANTIGENS OR ANTIBODIES

[75] Inventors: Johann Eibl, Vienna; Helmut Aicher, Obersiebenbrunn, both of Austria

[73] Assignee: Immuno Aktiengesellschaft für chemisch-medizinische Produkte, Vienna, Austria

[21] Appl. No.: 936,500

[22] Filed: Aug. 24, 1978

Related U.S. Application Data

[62] Division of Ser. No. 824,507, Aug. 15, 1977, abandoned.

[30] Foreign Application Priority Data

Aug. 20, 1976 [AT] Austria .................................. 6185/76

[51] Int. Cl.³ ............................................. G01N 33/56
[52] U.S. Cl. ..................................... 422/71; 23/230.6; 23/920; 422/104; 424/1
[58] Field of Search ..................... 422/65, 102, 71, 104; 141/130; 73/425; 23/920, 230 B, 230.6; 424/1

[56] References Cited

U.S. PATENT DOCUMENTS

| 3,826,619 | 7/1974 | Bratu, Jr. et al. .................. 422/58 |
| 3,932,141 | 1/1976 | Beall ................................. 23/230 B |
| 3,951,605 | 4/1976 | Natelson .............................. 422/65 |
| 4,090,850 | 5/1978 | Chen et al. ......................... 422/102 |
| 4,154,796 | 5/1979 | Thorne ............................... 422/102 |
| 4,155,711 | 5/1979 | Zelagin .............................. 422/65 |
| 4,160,803 | 7/1979 | Potts .............................. 422/102 X |

*Primary Examiner*—R. E. Serwin
*Attorney, Agent, or Firm*—Brumbaugh, Graves, Donohue & Raymond

[57] ABSTRACT

In an arrangement for carrying out a radioimmunological method of determining both antigens and antibodies by examining samples of human body liquids by forming an antigen/antibody-complex with a radioactively labelled antibody, a micro-titer-plate is provided with recesses for accommodating a solution of said radioactively labelled antibody and to the sample to be examined. Carriers, in the form of elongated elements secured to a holding band, are loaded with unlabelled antigen and are contacted with the sample by being inserted in the recesses of the micro-titer-plate. The carrier is washed, and the radioactivity of the carrier is measured.

3 Claims, 3 Drawing Figures

APPARATUS FOR PERFORMING A RADIOIMMUNOLOGICAL METHOD OF DETERMINING ANTIGENS OR ANTIBODIES

This is a division of application Ser. No. 824,507, filed Aug. 15, 1977 and now abandoned.

BACKGROUND OF THE INVENTION

The invention relates to a radioimmunological method of determining antigens, in particular hepatitis-B-surface antigen, or antibodies in human body liquids, such as human plasma, human serum and fractions thereof, by forming an antigen/antibody-complex in which the antibody component is radioactively labelled.

Radioimmunotests—also called radioimmunoassays—initially were used for demonstrating the presence of hormones. The system described by Yalow and Berson (J. Clin. Invest. 1157–1175, 1960, "Immunoassay of endogenous plasma insulin in man") is based on the ability of a highly specific antibody to bind its radioactively labelled antigen and on the inhibition of this reaction by the unlabelled (sample) antigen whose presence is to be demonstrated. Thereupon the radioactive antigen which has not been bound is quantitatively removed from the test mixture and the bound activity is measured with a suitable appliance. The difficulty inherent in carrying out such determinations or demonstrations consists in the quantitative separation of the components not reacted in the complex formation. For the separation, the methods of paper electrophoresis, precipitation with a second antibody (double antibody methods), precipitation of the antigen/antibody-complex with polyethyleneglycol, adsorption of the free antigen on activated carbon, or separation by reaction on a solid phase are eligible. In the latter case, the solid phase is produced by a covalent bond of a reaction component on either activated cellulose, Sephadex or Sepharose (Wide and Porath, Biochem. Biophys. Acta 130, 257–260, 1966, "Radioimmunoassay of proteins with the use of Sephadex coupled antibodies"), or by adsorption of a reaction partner to a suitable surface, preferably plastics materials (Catt, Niall and Tregear, Biochem. J., 100, 31C–33C, 1966, "Solid-phase radioimmunoassay of human growth hormone").

For demonstrating hepatitis-B-surface antigen ($HB_sAG$) and the corresponding antibody (anti$HB_sAB$) by means of radioimmunoassays, hitherto the following methods have been known:

1. Ausria I, Ausria II, Ausab (Abbott Laboratories). These methods work according to the so-called sandwich-principle.

In the Ausria-I-method a tube loaded with antibody is filled with the sample to be examined. After incubation an antibody/antigen-complex (AB-AG) forms, if antigen is present, and the antibody component is fixed to the tube. Then the liquid is removed and the tube is washed and treated with a solution of radioactively labelled antibody. After a repeated incubation, an antibody/antigen/labelled antibody (AB-AG-AB*) complex forms. The tube is washed again and the radioactivity of the AB-AG-AB* complex (sandwich-complex) is determined. The antibody is labelled by installing radioactive iodine ($^{125}I$) in a known manner. The Ausria-II-method uses ball-shaped solid carriers instead of tubes. The Ausab-method is largely similar to the Ausria-methods. Here, however, an inverted set-up of the sandwich-complex is chosen, i.e. AG-AB-AG*;

2. Riausure-method of Electro Nucleonics Laboratories. With this method a sandwich-complex is formed in a similar manner as with the Ausria-II-method, but glass particles are used as solid carriers instead of balls;

3. Combi-RIA-Biotest-method. Here the sample to be examined for antigen is mixed with an adjusted antibody and the mixture is transferred into a small cup that is coated with antigen. After incubation of the sample and washing of the cup, radioactive antigen is added. Then the sample is incubated again and the cup is washed again.

This is also one of the sandwich-methods, in which complicated washing and separating operations are necessary. If the samples contain only little antigen, all these methods are inaccurate.

SUMMARY OF THE INVENTION

The present invention aims at avoiding the above-described disadvantages and difficulties and has as its object to provide a determination method, and an arrangement that is suitable for carrying it out, in which complicated separating and washing procedures are avoided and the determination is more precise.

According to the invention, this object is achieved in that a solution of the radioactively labelled antibody is added to the sample to be examined for a content of antigen or antibody, and then a solid carrier loaded with unlabelled antigen is contacted with the sample liquid, whereupon, after washing of the carrier, the radioactivity of the carrier is measured.

In the method according to the invention, the evaluation is carried out by directly measuring the radioactivity on the solid phase—not by measuring the radioactivity of the supernatants as has been the case with the radioimmunoassays hitherto known. Beside the work saved by avoiding centrifuging and pipetting, the highest count rates are obtained in the realm of the negative or only very slightly positive samples, which constitutes a substantial improvement in the accuracy of the assay results.

If the sample that is examined does contain antigen, it reacts with the radioactively labelled antibody. In the next step, in which the carrier loaded with unlabelled antigen is immersed in the reaction liquid, only that part of the labelled antibody which has not been used up by the antigen content of the sample, can react with the antigen adsorbed on the carrier. Thus after washing of the carrier, a certain amount of bound radioactivity will be found, which is inversely proportional to the antigen content in the sample.

If the sample to be examined does not contain antigen, but does contain antibody, the antibody content in the sample liquid will be increased. Thus, during the first incubation no reaction will take place. When in the next step the solid carrier loaded with unlabelled antigen is contacted with the sample liquid, there results a competition between the unlabelled and the labelled antibody in the reaction with the adsorbed antigen on the carrier. This competition means that in this case a certain amount of radioactivity will be found on the washed carrier, which amount is again inversely proportional to the antibody content of the sample that has been examined. When in serial examinations of samples a reduced radioactivity is found as compared to a control sample which contains neither antigen nor antibody, it is known that the respective sample contains either antigen or antibody, but it is not known which one is present. In order to find this out, a so-called differential diagnosis is carried out, in which a second sample of the same kind is contacted with a second carrier and incubated. The carrier is washed and in a further step it is contacted with radioactively labelled antibody and incubated. If this measurement of the radioactivity gives a higher count rate, this means that no antibody was in the sample, but antigen was, since all the adsorbed antigen has been used up in forming the antigen/antibody-complex. If a reduced count rate is found, however, this means that during the incubation the antibody of the sample was used with the adsorbed antigen for forming the antigen/antibody-complex and only a few binding places were free for the labelled antibody on the carrier loaded with antigen.

Advantageously, a radioactively labelled antibody that has been stabilized with heparin is used.

Suitably, the incubations are carried out at a temperature of between 18° and 45° C. for a period of 30 minutes to 15 hours, preferably at 45° C. for a period of 60 minutes.

The method of the invention is especially suitable for the determination of $HB_sAG$ and $antiHB_sAB$. In principle, however, it can be used for demonstrating all antigens against which specific antibodies can be developed. This method is also suitable for demonstrating antibodies whose antigens are proteins or polypeptides, respectively, and which can be prepared in purified form. It can also be used—as the system $HB_sAG/antiHB_sAB$ shows—in the comparative rare case that sera of patients contain the antigen as well as the antibody. Further fields of application of the method of the invention are the determination of virus-antigens and the determination of blood coagulation factors, in particular the factor-VIII-protein.

The invention also relates to an arrangement for carrying out the above-described method by using a micro-titer-plate having recesses for accommodating the samples to be examined with solid carriers loadable by a complex former. This arrangement is characterized in that the carriers comprise platelets or pins which are secured to a holding band and are insertable in the recesses of the micro-titer-plate.

Advantageously, between the holding band and each individual platelet a groove is provided to form a predetermined breaking point. Advantageously, the carrier platelets can be made of plastics material.

The carrier can be loaded by treating it with an antigen solution by immersion for a period of between 24 and 60 hours.

BRIEF DESCRIPTION OF THE DRAWINGS

The arrangement for carrying out the method of the invention shall now be described in more detail by way of example only and with reference to the accompanying drawings, wherein.

DESCRIPTION OF EXEMPLARY EMBODIMENTS

Figure 1:
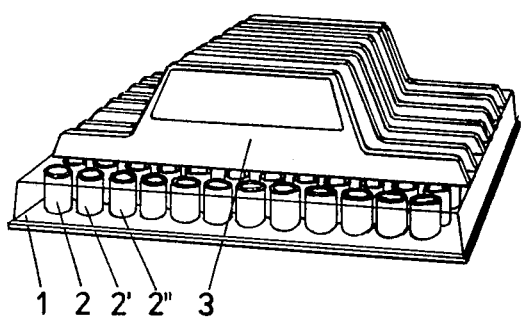
FIG. 1 is a perspective view of the apparatus according to the present invention.
Figure 2:
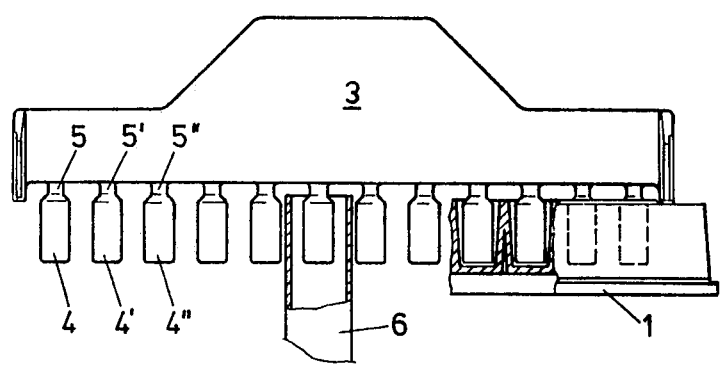
FIG. 2 is a front elevation of a carrier.

The arrangement according to the present invention comprises a micro-titer-plate 1 provided with a number of rows, e.g. twelve, of recesses 2, 2', 2" . . . for examining the sample. Furthermore, holding bands 3 of the arrangement are combined with one row of numbered platelets 4, 4', 4" . . . to form comb-like carriers. The platelets are arranged to correspond to the number of recesses of one row of the micro-titer-plate. The platelets 4, 4', 4" . . . are secured to the holding band 3 by means of neck pieces 5, 5', 5" . . . , whose cross-section is smaller than that of the platelets. These neck pieces form pre-determined breaking points. When the platelets have reacted according to the above-described method with the sample to be examined in the recesses of the micro-titer-plate, the platelets are broken off and dropped into counting tubes 6, as indicated in FIG. 2.

The following examples are intended for a further explanation of the method of the invention in connection with the above described arrangement:

EXAMPLE 1

Determination of $HB_sAG$ and $antiHB_sAB$

With this examination, either the $HB_sAG$ or the $antiHB_sAB$ may be contained in the sample of a human body liquid to be examined, or none of the two substances may be contained. In a first assay step 0.2 ml of the material to be examined are incubated for approximately 60 minutes at 45° C. in an incubator with purified $^{125}I$-labelled $antiHB_sAB$ (0.1 ml contains about 0.1 mcCi) in a micro-titer-plate, and two $HB_sAG$ positive, three $HB_sAG/antiHB_sAB$-negative and seven $HB_sAG$ weakly positive control samples are carried along. At the end of this incubation, the comb-like carriers coated with $HB_sAG$ are introduced into the pre-incubated mixtures and are further incubated at 45° C. for between 90 and 120 minutes. Thereupon the comb-like carriers are removed from the test solutions and washed in a tub with water from the main. The individual test platelets on the comb-like carriers are transported into the test tubes by breaking them off at the pre-determined breaking points. In a gamma-spectrometer the bound radioactivity on the individual platelets is determined. On the control samples (1 to 12) carried along and on the samples (13 to 24) to be examined, the following values were obtained:

| Sample | time in min. | cpm |         |
|--------|--------------|------|---------|
| 1      | 1.00         | 684  |         |
| 2      | 1.00         | 672  |         |
| 3      | 1.00         | 4644 |         |
| 4      | 1.00         | 4148 |         |
| 5      | 1.00         | 4087 |         |
| 6      | 1.00         | 1974 |         |
| 7      | 1.00         | 1997 |         |
| 8      | 1.00         | 1846 |         |
| 9      | 1.00         | 2035 |         |
| 10     | 1.00         | 1942 |         |
| 11     | 1.00         | 2455 |         |
| 12     | 1.00         | 1598 |         |
| 13     | 1.00         | 433  | positive |
| 14     | 1.00         | 340  | positive |
| 15     | 1.00         | 4996 |         |
| 16     | 1.00         | 4020 |         |
| 17     | 1.00         | 2946 |         |
| 18     | 1.00         | 2673 |         |
| 19     | 1.00         | 2445 |         |
| 20     | 1.00         | 2822 |         |
| 21     | 1.00         | 1317 | positive |
| 22     | 1.00         | 1550 | positive |
| 23     | 1.00         | 3991 |         |
| 24     | 1.00         | 4052 |         |

Samples 1 and 2 are strong $HB_sAG$ positive control serum, samples 3 to 5 are $HB_sAG/antiHB_sAB$-negative control serum and samples 6 to 12 are $HB_sAG$-weak-positive control serum. The average values were calculated from these three groups and with the seven $HB_sAG$-weak-positive control sera 20% was added to or subtracted from, respectively, the average value. It is required that at least six of the seven samples be within these calculated limits. If one sample is outside the two limiting values (in the present series sample No. 11), its value is not taken into consideration in the evaluation. The average value of the remaining six samples plus 20% is taken as the limiting value. Each sample having a lower count rate than this limiting value is to be considered positive and is indicated in the table as positive (samples 13, 14, 21, 22).

After this first test step it has to be determined whether the positive reaction was caused by $HB_sAG$ or by $antiHB_sAB$. For providing the differential determination, a second test set-up is carried out in the following manner:

Samples with 0.2 ml each are pre-arranged in the micro-titer-plate and incubated with $HB_sAG$-coated comb-like carriers for 60 minutes at 45° C. Thereafter the carriers are removed from the sample solutions, and as described above, washed and incubated for further 60 to 120 minutes in 0.2 ml of a 1 plus 1 dilution of the $^{125}I$-labelled $antiHB_sAB$ in a physiological salt solution. Then the comb-like carriers are washed a second time and examined in a gamma-spectrometer as indicated above. It should be kept in mind that in the first test series in the first incubation a specific inhibition of the radioactively labelled antibody takes place if $HB_sAG$ is present in the sample, while the total antibody amount in the reaction mixture is increased if $antiHB_sAB$ is present in the sample. After insertion of the comb-like carriers, the radioactively labelled antibody not bound to the sample antigen is bound to the surface of the test platelets, and if $HB_sAB$ is present, a part of the sample antibody as well as a part of the radioactively labelled antibody will be fixed to the surface of the comb-like carriers. As compared to $HB_sAG/antiHB_sAB$-negative control samples a reduction of the count rates on the test platelets will be found if $HB_sAG$ is present in a sample as well as if $HB_sAB$ is present in a sample. In the differential determination, no immunological reaction will take place during the incubation of the comb-like carriers with the samples if $HB_sAG$ is in the samples, or if the samples are $HB_sAG/antiHB_sAB$-negative. If $antiHB_sAB$ is present in the sample, it can occupy the antigen binding places on the comb-like carrier.

If the comb-like carriers are then washed and incubated again, this time with $^{125}I$-labelled $antiHB_sAB$, the radioactive material can only occupy the antigen binding places on the solid phase which are still free. Thus, if $antiHB_sAB$ is present in the samples, the count rates are reduced. If $HB_sAG$ is present or in case of $HB_sAG/antiHB_sAB$-negative samples, the count rates remain high.

The results found are listed in the following table:

| Sample | time in min. | cpm |
|---|---|---|
| 1 | 1.00 | 3866 |
| 2 | 1.00 | 3716 |
| 3 | 1.00 | 3949 |
| 4 | 1.00 | 3799 |
| 5 | 1.00 | 3964 |
| 6 | 1.00 | 1435 |
| 7 | 1.00 | 1504 |
| 8 | 1.00 | 1605 |
| 9 | 1.00 | 1627 |
| 10 | 1.00 | 1482 |
| 11 | 1.00 | 1449 |
| 12 | 1.00 | 1448 |
| 13 | 1.00 | 3951 positive $HB_sAG$ |
| 14 | 1.00 | 4026 positive $HB_sAG$ |
| 15 | 1.00 | 3910 |
| 16 | 1.00 | 3996 |
| 17 | 1.00 | 3884 |
| 18 | 1.00 | 3843 |
| 19 | 1.00 | 3917 |
| 20 | 1.00 | 3871 |
| 21 | 1.00 | 363 positive $antiHB_sAB$ |
| 22 | 1.00 | 1335 positive $antiHB_sAB$ |
| 23 | 1.00 | 3776 |
| 24 | 1.00 | 3778 |

As control sera Nos. 1 and 2, $HB_sAG$-weak-positive serum was used; Nos. 3 to 5 are $HB_sAG/antiHB_sAB$-negative sera and the control samples Nos. 6 to 12 are $antiHB_sAB$-positive sera. Again, the average values of these three groups and the limiting value of the $antiHB_sAB$-positive groups were calculated as above. Each sample, whose count rate is below this limiting value is to be considered as positive as regards $antiHB_sAB$ (samples 21, 22). Samples 13 and 14 gave high count rates and must be taken to be $HB_sAG$-positive. All the remaining samples that gave high count rates in both reactions, are $HB_sAG$ and $antiHB_sAB$ negative.

EXAMPLE 2

Determination of alpha-fetoprotein (AFP)

Alpha-fetoprotein that has been purified by gel chromatography is used for coating the comb-like carriers. Anti-alpha-fetoprotein-antibody is purified over an immunsorbens (BRCN-Sepharose) and labelled with $^{125}I$. The normal levels are between 0 and 40 ng/ml serum. With certain liver diseases and with carcinomas the values are increased to from 100 ng/ml up to 1000 ng/ml.

The quantitative determination of the antigens or antibodies, respectively, is carried out in the following manner:

Instead of the control sera, a dilution series of the antigen to be determined is carried along. The dilution series for obtaining a calibration curve are prepared as follows: Preferably geometrical dilutions of the standard in the negative control serum are chosen and, as control samples, negative control serum and the labelled antibody alone are inserted. The samples with the pure antibody give the values of the maximum binding capacity of the set-up. The samples with the negative control serum give the values of maximum binding if negative samples are present. With an increasing concentration of the standard antigen in the calibration curve, the bound activity falls proportionately to the concentration. All the control samples are to be set up in double determination, preferably in triple determination.

Figure 3:
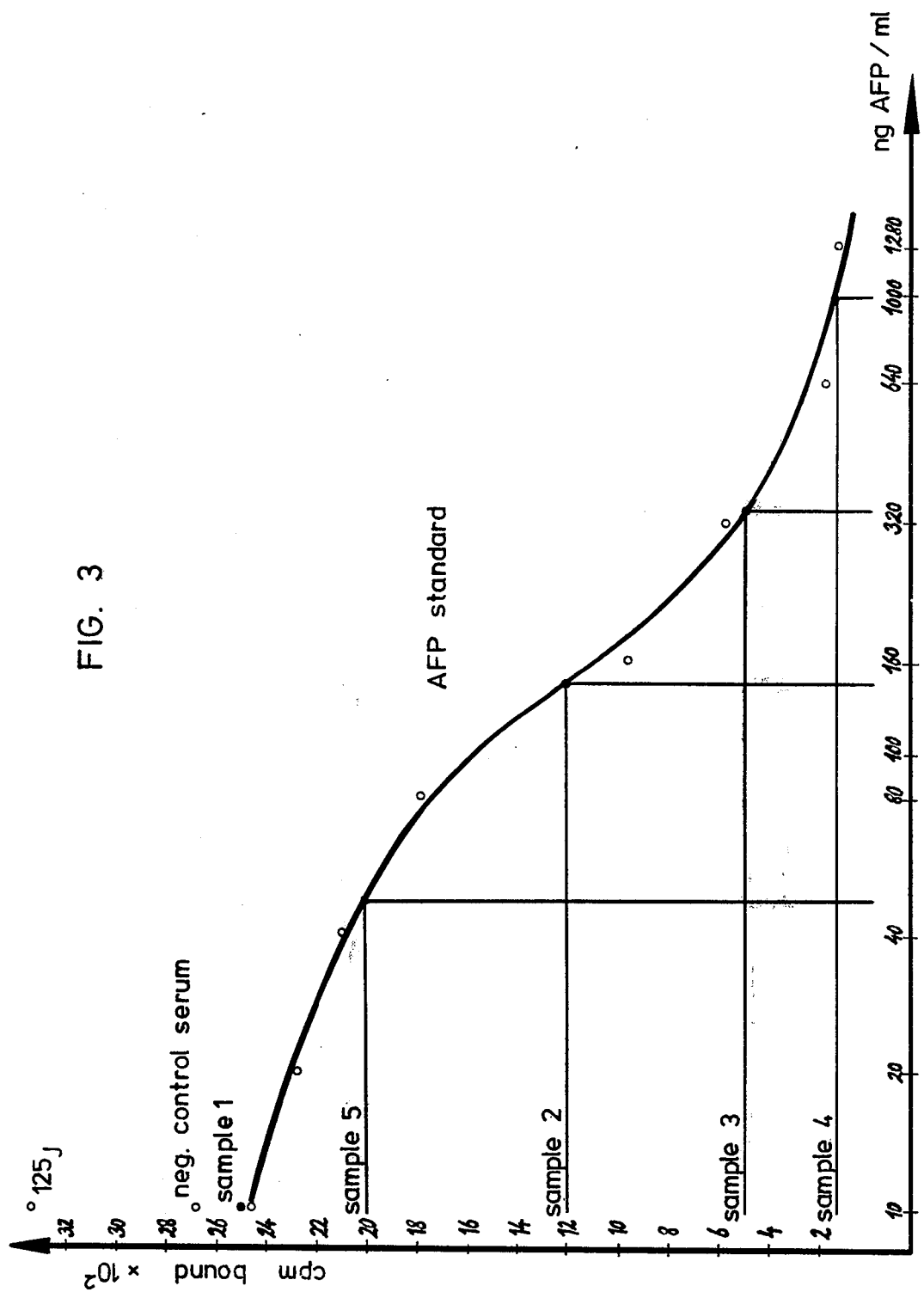
FIG. 3 is a calibration curve for the apparatus of FIGS. 1 and 2.

A calibration curve obtained from the following individual values is illustrated in the enclosed diagram (FIG. 3) and denoted with AFP-standard:

| Individual values | Calibration Curve | |
|---|---|---|
| 10 ng AFP | $c_1 = 2516$ | |
| | $c_2 = 2488$ | $\bar{c} = 2460$ cpm |
| | $c_3 = 2376$ | |
| 20 ng | $c_1 = 2276$ | |
| | $c_2 = 2360$ | $\bar{c} = 2287$ cpm |
| | $c_3 = 2225$ | |
| 40 ng | $c_1 = 2100$ | |
| | $c_2 = 2045$ | $\bar{c} = 2100$ cpm |
| | $c_3 = 2156$ | |
| 80 ng | $c_1 = 1673$ | |
| | $c_2 = 1515$ | $\bar{c} = 1581$ cpm |
| | $c_3 = 1555$ | |
| 160 ng | $c_1 = 983$ | |
| | $c_2 = 875$ | $\bar{c} = 955$ cpm |
| | $c_3 = 1006$ | |
| 320 ng AFP | $c_1 = 614$ | |
| | $c_2 = 588$ | $\bar{c} = 567$ cpm |
| | $c_3 = 499$ | |
| 640 ng AFP | $c_1 = 143$ | |
| | $c_2 = 205$ | $\bar{c} = 171$ cpm |
| | $c_3 = 166$ | |
| 1280 ng | $c_1 = 122$ | |
| | $c_2 = 166$ | $\bar{c} = 126$ cpm |
| | $c_3 = 89$ | |
| negative control serum | $c_1 = 2625$ | |
| | $c_2 = 2783$ | $\bar{c} = 2707$ cpm |
| | $c_3 = 2712$ | |
| max. binding with $^{125}$I antibody | $c_1 = 3540$ | |
| | $c_2 = 3236$ | $\bar{c} = 3340$ cpm |
| | $c_3 = 3245$ | |

After the curve is created the test proceeds in the same manner as in the HB$_s$AG test given in Example 1.

The sample to be examined is incubated with the labelled antiserum and thereupon the comb-like carriers coated with AFP are inserted in the micro-titer-plates. After a further incubation the comb-like carriers are washed and the activity on the individual test platelets is determined in a gamma-spectrometer. The count rates found were as follows:

| Sample | | Sample | |
|---|---|---|---|
| 1 | $c_1 = 2525$ | 4 | $c_1 = 146$ |
| | $c_2 = 2481$ | | $c_2 = 135$ |
| | $c_3 = 2411$ $\bar{c} = 2472$ cpm | | $c_3 = 104$ $\bar{c} = 128$ cpm |
| 2 | $c_1 = 1142$ | 5 | $c_1 = 2017$ |
| | $c_2 = 1276$ | | $c_2 = 1965$ |
| | $c_3 = 1217$ $\bar{c} = 1212$ cpm | | $c_3 = 2034$ $\bar{c} = 2005$ cpm |
| 3 | $c_1 = 475$ | | |
| | $c_2 = 512$ | | |
| | $c_3 = 489$ $\bar{c} = 492$ cpm | | |

They were plotted in the calibration curve diagram and gave the following result:
Sample:
1—negative
2—140–145 ng
3—380 ng
4—approximately 1000 ng
5—48 ng The following examples list other antigen/antibody determinations that can be made according to the invention.

EXAMPLE 3

Determination of HCG (human chorionic gonadotropin)

HCG, a glycoprotein hormone, is used for coating the comb-like carriers and antiHCG AB is radioactively labelled with $^{125}$I. The normal values lie at 2 mIU/ml and if carcinomas occur, the values are increased up to 100 mIU/ml. The determination of the HCG is especially valuable when observing the chemotherapy.

EXAMPLE 4

Determination of gastrin

Gastrin is used for coating the comb-like carriers. As antibody solution an antigastrin-AB-solution labelled with $^{125}$I is prepared.

The determination of gastrin is of increasing importance, since it is directly produced by tumors. Furthermore, increased gastrin levels are found in case of a deficient acid secretion of the stomach.
Determination of antibodies.

EXAMPLE 5

Determination of IgE

IgE is a specific immunoglobulin, the presence of which may be a hint to the presence of atopic allergies. In this case an antiIgE is bound to the comb-like carriers, which acts as antigen. If the samples are pre-incubated with a labelled IgE and then the carriers are inserted, the bound activity on the carriers is inversely proportional to the IgE concentration in the material under examination.

EXAMPLE 6

Determination of allergen

If instead of the antiIgE a specific allergen (e.g. penicillin) is coupled to the comb-like carrier, the same assaying procedure can be carried out allergen-specifically relative to this allergen with the help of labelled antibodies.

EXAMPLE 7

Determination of tetanus antibody

Tetanus antibodies are bound to the comb-like carriers. The samples are pre-incubated with $^{125}$I-labelled tetanus toxin and thereafter the comb-like carriers are inserted. The presence of tetanus antibodies in the sample is found because of the reduction of the count rates as compared to control samples.

EXAMPLE 8

Determination of DNA-antibody (DNS-antibody)

The determination of anti-DNA-antibody titers is a sensitive method of demonstrating lupus erythematodes visceralis and allows a differential determination relative to collagenoses of a different genesis. The comb-like carriers are coated with anti-DNA-antibody. $^{125}$I-labelled DNA is incubated with the sample and thereupon the comb-like carrier is inserted. The presence of anti-DNA-antibodies is shown by reduced count rates on the test platelets.

EXAMPLE 9

Determination of immune complexes

Method (a) The comb-like carriers are coated with heat-aggregated IgG; (IgG is aggregated by incubation at 60° C. after 20 minutes). This material acts immunologically like immune complexes. $^{125}$I-labelled rheumatoid factor is pre-incubated with the sample and is bound to immune complexes. Then the comb-like carriers are inserted. The tracer which has not been used up is bound to the test platelets. Low count rates on the test platelets indicate the presence of immune complexes in the sample.

Method (b) The $^{125}$I-labelled rheumatoid factor can be replaced by $^{125}$I-labelled Clq (first component of the complement system). The reaction mechanism remains the same.

The determination of antigen/antibody-complexes increases in importance, since these complexes can be associated with the pathogenesis of a number of aspects of cases, such as arthritis, systemic lupus erythematosus, glomerulonephritis, hepatitis and maybe cancer.

EXAMPLE 10

Simultaneous determination of antigen and antibody

The occurrence of antibodies to the antigen to be examined is unusual in the common radioimmunoassay, since in most cases very small antigens (e.g. hormones) are determined, which by themselves do not act antigen or which, as the body's own substances, do not produce antibodies, respectively. However, since to an increasing extent also high molecular pathogenic substances are examined with these methods, in such cases it is necessary to count on an occasional occurrence of antibodies to these substances in individual samples.

What we claim is:

1. In an arrangement for carrying out a radioimmunological method of determining antigens or antibodies of the type including a micro-titer-plate having recesses for accommodation of the samples to be examined and solid carriers loadable with a complex former, the improvement which is characterized in that the solid carriers are elongated plate-like elements and that a holding band is provided to which said elongated plate-like elements are secured, a neck piece of smaller cross section than the elongated elements is provided between the holding band and each elongated element to form pre-determined breaking points, the elongated plate-like elements are insertable in the recesses of the micro-titer-plate.

2. An arrangement as set forth in claim 1, wherein said carriers are made of plastics material.

3. An arrangement as set forth in claim 1, wherein said carrier has been loaded with antigens and antibodies by immersion in an antigen solution for between 24 and 60 hours.

* * * * *